US012667699B2

(12) United States Patent
Van Damme et al.

(10) Patent No.: US 12,667,699 B2
(45) Date of Patent: Jun. 30, 2026

(54) CATHETER FIXATION DEVICE

(71) Applicant: BEDAL NV, Diepenbeek (BE)

(72) Inventors: Alexander Van Damme, Zoersel (BE);
Simon Callaerts, Leuven (BE)

(73) Assignee: BEDAL NV, Diepenbeek (BE)

( * ) Notice: Subject to any disclaimer, the term of this
patent is extended or adjusted under 35
U.S.C. 154(b) by 738 days.

(21) Appl. No.: 18/003,379

(22) PCT Filed: Jun. 28, 2021

(86) PCT No.: PCT/EP2021/067735
§ 371 (c)(1),
(2) Date: Dec. 27, 2022

(87) PCT Pub. No.: WO2022/002870
PCT Pub. Date: Jan. 6, 2022

(65) Prior Publication Data
US 2023/0310809 A1 Oct. 5, 2023

(30) Foreign Application Priority Data

Jun. 29, 2020 (EP) .................................... 20182939

(51) Int. Cl.
*A61M 25/02* (2006.01)
(52) U.S. Cl.
CPC ....... *A61M 25/02* (2013.01); *A61M 2025/024*
(2013.01); *A61M 2025/0266* (2013.01)

(58) Field of Classification Search
CPC ............ A61M 25/02; A61M 2025/024; A61M
2025/028; A61M 2025/0246
See application file for complete search history.

(56) References Cited

U.S. PATENT DOCUMENTS

| | | | |
|---|---|---|---|
| 2006/0247577 A1 | 11/2006 | Wright | |
| 2012/0316506 A1 | 12/2012 | Sonderegger | |
| 2015/0038912 A1 | 2/2015 | Karim et al. | |
| 2015/0367102 A1* | 12/2015 | Andino ................. | A61M 25/02 604/179 |
| 2020/0297974 A1* | 9/2020 | Van Damme ......... | A61M 25/02 |

FOREIGN PATENT DOCUMENTS

| | | |
|---|---|---|
| WO | 2013021160 A1 | 2/2013 |
| WO | 2014149668 A1 | 9/2014 |
| WO | 2019063847 A1 | 4/2019 |

OTHER PUBLICATIONS

International Search Report and Written Opinion mailed Jul. 16,
2021 in reference to co-pending European Application No. PCT/
EP2021/067735 filed Jun. 28, 2021.

* cited by examiner

*Primary Examiner* — Deanna K Hall
(74) *Attorney, Agent, or Firm* — Dinsmore & Shohl LLP

(57) ABSTRACT

The present invention relates to means for fixating different
sizes of catheters comprising a luer-lock, which are used in
healthcare and in particular to means for fixating such
catheters to a living creature.

15 Claims, 3 Drawing Sheets

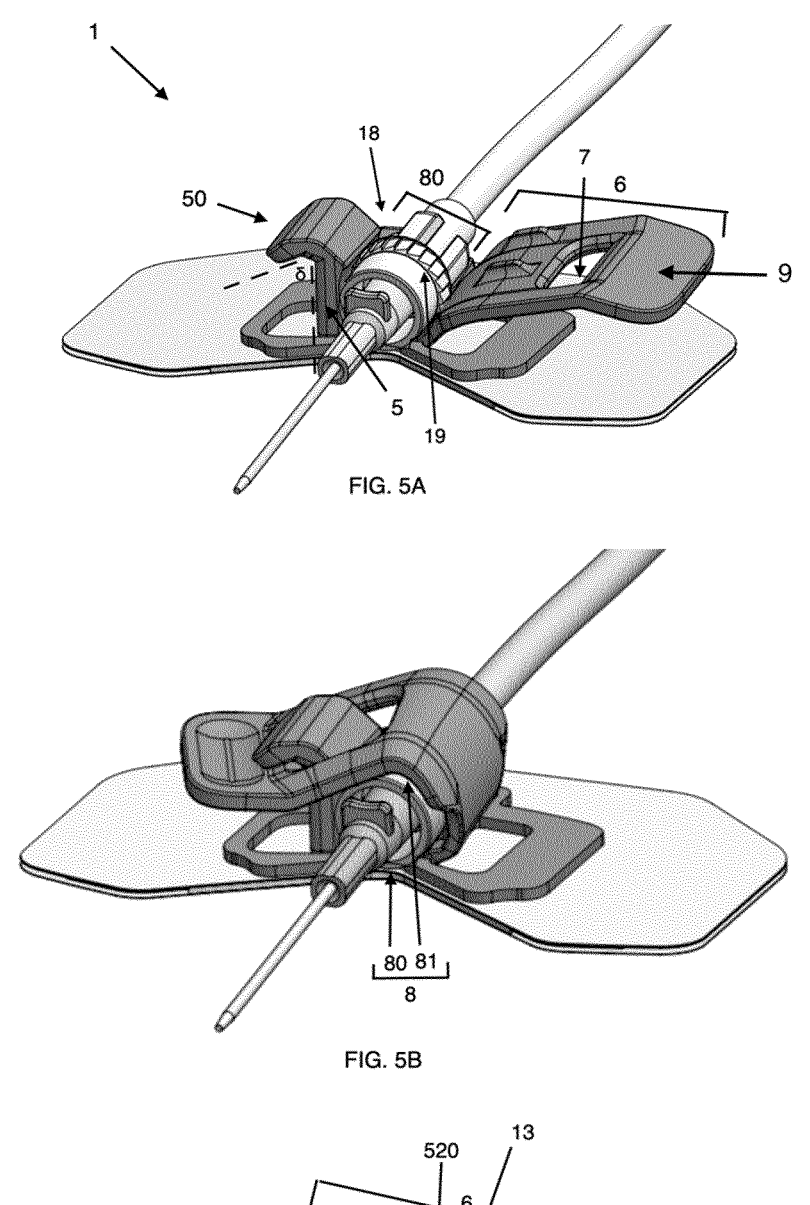
FIG. 5A
FIG. 5B
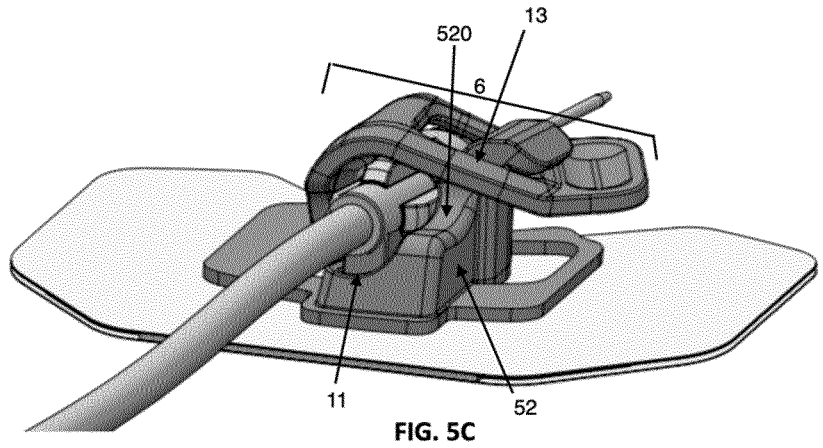
FIG. 5C

CATHETER FIXATION DEVICE

CROSS REFERENCES TO RELATED APPLICATIONS

This application is a national-stage application under 35 U.S.C. § 371 of International Application No. PCT/EP2021/067735, filed Jun. 28, 2021, which International Application claims benefit of priority to European Patent Application No. 20182939.7, filed Jun. 29, 2020.

FIELD OF THE INVENTION

The present invention relates to means for fixating different sizes of catheters comprising a luer-lock, which are used in healthcare and in particular to means for fixating such catheters to a living creature.

BACKGROUND TO THE INVENTION

In healthcare, a catheter is used to provide an access to the human body for delivery of medicinal drugs, parenteral nutrition, blood or blood components or other liquids or for drainage of a bodily fluid. A catheter is typically used for patients that are ill or during the performance of surgical procedures. Depending on the goal which is desired to be achieved and sometimes also depending on the patient or his/her medical condition, different catheters and different application methods can be selected. A specific type of catheters are peripheral intravenous catheters, these are connected to an infusion line or extension line with a luer-lock, which generally comprise a male and a female luer-lock connecting part. The tabbed hub on the female part generally screws into the screw threads of the male fitting in order to achieve a leak-free connection. Other variants are luer-slip fittings, both male and female parts thereof not comprising any screw threads but rather being pressed and held together by friction.

Further types of catheters include midline catheters, central venous catheters and epidural catheters.

A common disadvantage of the securement of such catheters to a patient is the burden for patients in terms of wearing comfort. For example, excessive movement whilst a catheter or part thereof is applied to the human body may be difficult to nearly impossible as the position of the catheter within the body should remain fixed under all circumstances. Accidental catheter removal, upon the exertion of a pulling force, should be avoided. Also, a change in position of the catheter (e.g. catheter dislocation or migration) may prevent proper operation and in some circumstances could even lead to dangerous or life-threatening situations. Therefore, a proper fixation of the catheter is of crucial importance to prevent critical situations and to allow patients to move more freely.

Moreover, when catheters involve luer-lock portions, an adequate fixation thereof upon the human body may become even more difficult as those luer-lock portions form an embossement of the catheter tubing, resulting in varying diameters of the catheter along the length of the catheter. Moreover, when the surface of the luer-lock portion is irregular, proper fixation is even more difficult.

Adequate fixation of catheters can be achieved using catheter fixation devices. These stabilization devices positively influence the lifetime of the catheter, decrease the number of catheter fixation procedures and the number of complications (e.g. phlebitis, extravasion or infections), all of which have been demonstrated in the scientific literature.

A number of known devices (e.g. US20120316506, US2006247577) are bulky and difficult to secure.

The securement of medical articles, such as catheters, comprising a luer-lock portion generally asks for more complex fixation devices.

Besides that, a number of known fixation devices fail to adequately prevent small longitudinal movements of the catheter, also known as micro-pistoning, leading to increased risk of infections. Other known medical devices require complicated and lengthy application procedures, such as for example a large number of foils which are to be removed prior to application. The longer and the more difficult the application of these fixation devices is, the longer it takes to tightly secure the catheter after insertion into the patient. Other known medical devices require several medical devices having different sizes and variants to be able to stabilize the different available catheter and luer lock variants.

Moreover, the locking mechanism of a number of devices requires two hands to operate. This may become complicated, especially when the catheter is already inserted in the patient and a proper fixation of the catheter within the fixation device is desired without excessive movement of the catheter.

Therefore, there is a continuous need in the art for means for improved securement and fixation of different types of catheters, in particular catheters containing a luer-lock portion, being compact and easy lockable while providing a sufficient amount of movement inhibition of the catheter.

The current invention discloses an easy lockable fixation device allowing for a tight fix of different types and sizes of catheters, more specifically those having a luer-lock, with the advantage that 1 single device is able to be used on a wide variety of catheter and luer lock sizes and variants.

SUMMARY OF THE INVENTION

In a first aspect, a medical device for securing a medical article to a living creature containing a luer-lock comprises: a body member having a first side adapted to be removably attached to the living creature, a second side opposite said first side, said second side provided with a retaining post, a first channel portion, a retaining strap attached to the body member, having a retaining segment comprising an opening, said opening being adapted to enclose at least part of said retaining post in an engaged position, a handling segment for manipulating said retaining strap between the disengaged position and the engaged position and a second channel portion, wherein said first channel portion and said second channel portion cooperate to form a channel in the engaged position, said channel being adapted to receive at least a portion of the luer-lock and characterized in that the medical article and the retaining strap cooperate to retain the retaining strap in the engaged position.

In a following aspect, the retaining strap of said medical device is an integral part of said body member.

In a next aspect, the retaining post of said medical device comprises a fluidum filled chamber.

In yet another aspect, the retaining post of said medical device further comprises an abutment angled in a horizontal plane relative to the retaining post.

In a further aspect, the abutment of said medical device grips behind an inner edge of the opening when the retaining strap is manipulated to the engaged position, retaining the retaining strap in the engaged position.

In a next aspect, the retaining strap of said medical device further comprises at least one protrusion exerting an inward pressure upon at least a portion of the luer-lock.

In a next aspect, said medical device further comprises a supporting structure having a deformable fluidum filled chamber, wherein said supporting structure is in line with said first channel portion in order to further support at least part of the medical article.

In a further aspect the tension exerted upon said medical device by the retaining strap is distributed over a first part and a second part of said retaining strap, wherein the tension exerted by at least said second part aids in preventing an upward movement of said medical article.

In yet another aspect, the maximum thickness of a central point of the first channel portion of said medical device is about and between 0.5 to 3 mm.

In a next aspect, the channel of said medical device is angled relative to the longitudinal axis of the medical device to define an incident angle between the channel and the living creature.

In a next aspect, the incident angle of said medical device constitutes an angle of about 5-10°, in particular about 7°.

In a next aspect, the handling segment of said medical device is angled relative to the remaining parts of the retaining strap.

In a next aspect, the first side of said medical device comprises an adhesive material.

In a next aspect, the retaining post and the retaining strap of said medical device inhibit at least longitudinal movement of the medical article relative to the body member in the engaged position.

In a next aspect, use of said medical device for securing a catheter to a living creature is disclosed.

In a further aspect, a kit comprising said medical device, a medical article and optionally an adhesive foil is disclosed.

BRIEF DESCRIPTION OF THE DRAWINGS

FIG. 5A is a front perspective view of a medical device comprising a medical article, according to an embodiment of the present invention, wherein the medical device is in a disengaged position.

FIG. 5B is a front perspective view of a medical device comprising a medical article, according to an embodiment of the present invention, wherein the medical device is in an engaged position.

FIG. 5C is a rear perspective view of a medical device comprising a medical article, according to an embodiment of the present invention, wherein the medical device is in an engaged position.

DETAILED DESCRIPTION OF THE INVENTION

Figure 1:
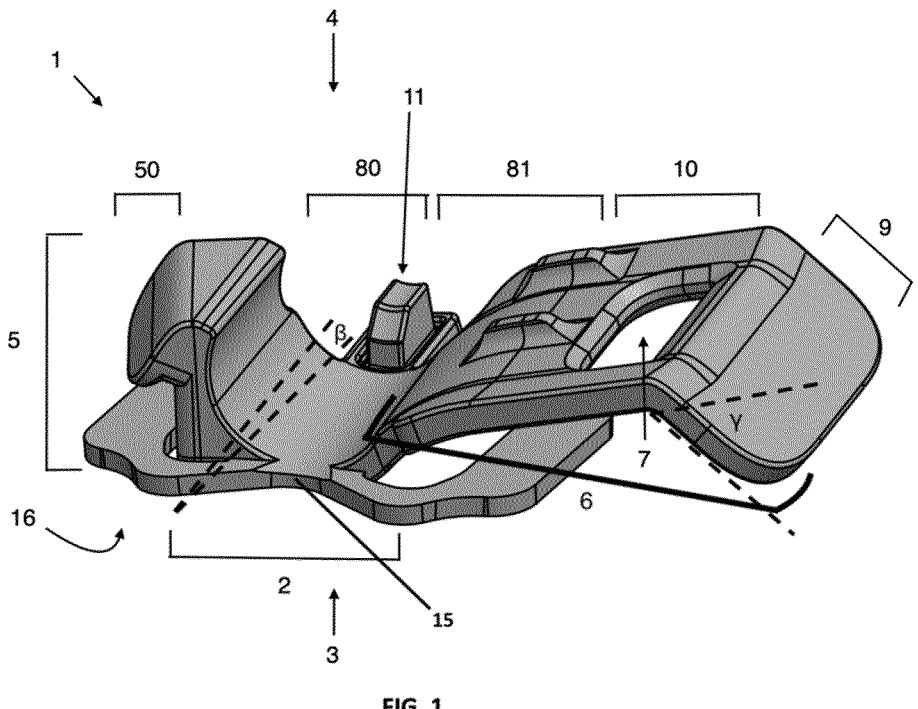
FIG. 1 is a perspective view of a medical device, according to an embodiment of the present invention.

The present invention will be described with respect to particular embodiments and with reference to certain drawings, but the invention is not limited thereto. The drawings, as further described, are only schematic and non-limiting. In the drawings, some of the elements may not be drawn to scale for illustrative purposes. The dimensions and the relative dimensions do not correspond to the actual reductions to practice of the invention.

Furthermore, the terms first, second, further and the like in the description and in the claims are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a product comprising A and B" should not be limited to devices consisting only of components A and B. It means that with respect to the present invention, the relevant components of the product are A and B, and that further components such as C may be present.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Besides that, when a part of the medical device is said to 'inhibit' movement and unless defined otherwise, the term 'inhibit' should be interpreted as partially or completely reducing movement. This term may alternatively be referred to as for example: "minimize", "constrain" or "impede".

Similarly, it is to be noticed that the term "integral part", also used in the claims, should be interpreted as being formed from a single part. Thus, the scope of the expression "an element A being an integral part of an element B" should be interpreted as two elements being formed from a single part, such as a single piece of material.

The following terms are provided solely to aid in the understanding of the invention. As used herein and unless otherwise specified, when a medical device is said to "secure a medical article to a living creature", it is meant that at least a portion of the medical article is fixed to and/or stabilized to and/or positioned onto the living creature. Securing the medical article typically hinders, or even completely prevents, translational and/or rotational movement (preferably both) of at least a portion of the medical article.

As used herein and unless otherwise specified, the term "living creature" is to be understood as the body of a living being, more in particular of human beings (e.g. patients) or animals. Securing the medical article to the living body advantageously reduces the risk of the medical article moving with respect to the body or even being accidentally removed therefrom.

As used herein and unless otherwise specified, the term "enclose" should be interpreted as to surround or close off an element within a two-dimensional space.

As used herein and unless otherwise specified, the term "deformable" should be interpreted as the capability of an object to be at least partially and temporarily reshaped when a certain amount of pressure is exerted upon that object.

As used herein and unless otherwise specified, the term "engaged position" (may hereinafter also be referred to as "closed position" or "activated position") should be interpreted as the position which enables an object to exercise its utility, with the opposite of the engaged position being the disengaged position. For example, if the retaining strap is brought into the engaged position while holding at least the luer-lock part of a catheter, it is meant that the medical device is clamping the catheter in order to inhibit movement thereof.

It is also an advantage of embodiments of the current invention that the medical device may be produced with techniques such as injection moulding while using only a single material.

It is a further advantage of embodiments of the current invention that at least the retaining strap may slightly stretch when being manipulated to the engaged position. This is particularly relevant when medical articles with slightly larger diameters are placed within the medical device.

It is an advantage of embodiments of the current invention that the medical device can be placed in close proximity to the insertion site of the catheter.

It is yet another advantage of embodiments of the current invention that the medical device may be made of a deformable material, thereby increasing the wearing comfort for the user.

It is a further advantage of embodiments of the current invention that the retaining strap can be brought repeatedly from a disengaged position to an engaged position, to allow repositioning or replacement of the infusion line with luer lock whilst the medical device is already attached to the living creature. This may be particularly useful when the infusion line with luer lock should be removed and replaced. In such cases, the medical device and catheter could stay in place, saving time and resources.

It is an advantage of embodiments of the current invention that catheters having different types and sizes of luer-locks can be secured within the medical device, such as for example luer-locks having a generally flat surface and luer-locks having a generally ribbed surface. Unless provided otherwise, the term "luer-lock" should be understood as standardized fittings for ensuring leak-free connections between a male and female part of a medical article (e.g. catheter tubing). Both parts may be secured by screwing the female fitting into the male fitting threads. On the outside, luer-locks may have a generally flat surface or a generally ribbed surface. In most cases, the luer-lock portion of the medical article forms an abutment (e.g. peripheral rim), contributing to the irregular shape of the medical article.

In preferred embodiments, the medical device is adapted to fix the luer-lock portion of the medical article. In other embodiments, the tubular portion of the medical article may be secured within the medical device.

It is a further advantage that a range of medical articles (e.g. needless connectors, infusion lines, connector lines) of which the luer-lock portion has varying diameters can be securely placed within a single medical device.

In some embodiments, the range of different diameters may be defined from about 1, 2, 3 to about 18, 19, 20 mm, more particular from about 4, 5, 6 to about 13, 14, 15 mm and even more particular from about 4,5; 5; 5,5 to about 13; 13,5; 14 mm.

Both the body member and the retaining strap comprise a deformable solid material, since both parts are integrally formed, enabling a certain variation of the channel diameter, which is especially useful when medical articles in the upper diameter range are placed within the medical device.

In preferred embodiments, when luer-lock portions are placed within the medical device with diameters deviating from the allowable diameter range, the retaining strap will not be securely kept in the engaged position. This serves as a unique control mechanism for the user when installing a catheter within the medical device. Only those catheters being suitable for placement, will be securely retained.

It is to be noticed that the term "medical article" should be given a broad interpretation as regards to its scope, thereby including medical articles such as catheters as such which may comprise different types of luer-lock parts, needless connectors (comprising a luer-lock), infusion lines, connector lines, . . . .

In any case, it should be noted that more specifically medical articles (e.g. catheters) comprising among other things at least one luer-lock part are included within the term "medical articles".

Furthermore, it should be appreciated that the medical devices according to embodiments of the current invention are adapted to secure medical articles by means of fixating at least a portion of the luer-lock of these medical articles, thereby inhibiting movement of the medical article when secured.

Besides that, it should be noted that "medical articles containing a luer-lock" also include needless connectors as these needless connectors equally comprise a luer-lock part.

In a first aspect, a medical device for securing a medical article to a living creature containing a luer-lock comprises: a body member having a first side adapted to be removably attached to the living creature, a second side opposite said first side, said second side provided with a retaining post, a first channel portion, a retaining strap attached to the body member, having a retaining segment comprising an opening, said opening being adapted to enclose at least part of said retaining post in an engaged position, a handling segment for manipulating said retaining strap between the disengaged position and the engaged position and a second channel portion, wherein said first channel portion and said second channel portion cooperate to form a channel in the engaged position, said channel being adapted to receive at least a portion of the luer-lock and characterized in that the medical article and the retaining strap cooperate to retain the retaining strap in the engaged position.

It is to be noticed that the term "channel" should be interpreted as merely comprising passage structures which are completely round (e.g. circular, oval, elliptical, tubular shaped), explicitly excluding semi rounded structures (e.g. semicircles, semi ovals, semi ellipses, U-shaped structures). Therefore, when a first channel portion and a second channel portion cooperate to form a channel, it is meant that both the first and second channel portions together form a completely round passage structure, which is defined as a "channel".

In preferred embodiments, the securement of the medical article entails that at least the luer-lock portion of the medical article (e.g. catheter), which is fixed within the channel of the medical device, remains at a fixed place when the medical device is in the engaged position, even when a force is exerted upon the medical article (e.g. a pulling force), for example a force exerted upon an infusion line or connector line.

In some embodiments, the first side of the body member may be removably attached to the living creature by means of an adhesive material. The adhesive material advantageously allows the first side to be easily fixed to the living creature. In preferred embodiments, the fixation may be reversible, such as by using a removable adhesive (e.g. tape, glue).

In some embodiments, the material of the body member may be selected from the list comprising: thermoplastic elastomers, polyurethane based gels, a foam, a gel, a tacky material, a rubber more general a deformable solid material.

In some embodiments, the cross-sectional shape of the retaining post may be selected from the list comprising: quadrangular, square, rectangular, oval or circular.

In preferred embodiments, both the retaining strap and the body member are made of a similar material and produced using for example injection molding. This way, the body member is integrally formed with the retaining strap, which may further positively influence the strength of the medical device as a whole.

In preferred embodiments, a deformable solid material may be used as a main material of at least the body member and the retaining strap which may be selected from the list comprising: a foam, a gel, a tacky material, a rubber or more generally a deformable solid material. The deformable solid material positively influences the wearing comfort of the patient, especially when the medical device is mounted on the patient's back and the patient would lie down in bed. The patient would, in this case, apply pressure on the medical device and the deformable solid material would allow the body member and the retaining strap to slightly deform in its entirety. As a result, the patient will experience less discomfort compared to medical devices comprising stiff, non-deformable materials. Besides that, a certain amount of deformability of the retaining strap simplifies the manipulation thereof in the engaged position.

In preferred embodiments, the handling segment, the retaining segment and the second channel portion lie in line with each other with the second channel portion closest to the body member. This way, the opening of the retaining segment can be positioned above retaining post in the engaged position, which simplifies the enclosing thereof. In some embodiments, the handling segment may further comprise a recess enabling to better grasp the handling segment.

In some embodiments, the retaining post may be at least partially filled with and/or made of a deformable solid material, which may be selected from the list comprising: thermoplastic elastomers, polyurethane based gels, a foam, a gel, a tacky material, a rubber or more generally a deformable solid material. In other embodiments, the shape of the retaining post may be adapted in such a way to be able to receive the shape of a specific type of catheters. Preferably, the shape of the channel is adapted in such a way to be able to receive the luer-lock part of catheters.

In some embodiments, the retaining post may comprise at least one supporting rib. The use of supporting ribs may increase the general stability and strength of the construction, which reduces the chance of collapse of said retaining post when applying pressure when for example lying upon the retaining post when wearing said medical device.

In some embodiments, the retaining post may be partially disconnected from the body member, so that the retaining post can be tilted without influencing the movement of the body member. Preferably, the connection between the retaining post and the body member will be cut at the transition area between both parts, thereby for example resulting in an incision or gap.

In a following aspect, the retaining strap of said medical device is an integral part of said body member.

In a next aspect, the retaining post of said medical device comprises a fluidum filled chamber.

In some embodiments, the fluidum filled chamber of the retaining post may be at least partially filled with a fluid, which may be selected from the list comprising: air or an oil. In other embodiments, said fluidum filled chamber may refer to a hollow structure having a certain amount of compressibility.

In yet another aspect, the retaining post of said medical device further comprises an abutment angled in a horizontal plane relative to the retaining post.

In preferred embodiments, the abutment is made of the same material as the retaining post. More preferably, the abutment is integrally formed with the retaining post. The abutment is generally present in order to immobilize the retaining strap. More specifically, an edge of the opening is secured underneath the abutment in such a way to tightly enclose the retaining post in the engaged position.

In a further aspect, the abutment of said medical device grips behind an inner edge of the opening when the retaining strap is manipulated to the engaged position, retaining the retaining strap in the engaged position.

In a next aspect, the retaining strap of said medical device further comprises at least one protrusion exerting an inward pressure upon at least a portion of the luer-lock.

In a next aspect, said medical device further comprises a supporting structure having a deformable fluidum filled chamber, wherein said supporting structure is in line with said first channel portion in order to further support at least part of the medical article.

Preferably, a tubular section of a catheter contacts the supporting structure. As used herein and unless otherwise specified, the term "contact" should be interpreted as the possibility of at least two elements being in a direct connection being preferably reversible. For example, when a tubular section of a catheter contacts the supporting structure, said supporting structure is shaped in such a way to closely adapt to the shape of the tubular section of the catheter.

In a further aspect the tension exerted upon said medical device by the retaining strap is distributed over a first part and a second part of said retaining strap, wherein the tension exerted by at least said second part aids in preventing an upward movement of said medical article.

In yet another aspect, the maximum thickness of a central point of the first channel portion of said medical device is about 0.5 to 3 mm, preferably, about 0.5 to 1 mm and even more preferably about 0.5 tot 0.6 mm, for example 0.57 mm. Because of said low maximum thickness, said medical device may easily be slid underneath a medical article (e.g. catheter), for example when such medical article is already fixed within the patient prior to the securement of the medical device.

In a next aspect, the channel of said medical device is angled relative to the longitudinal axis of the medical device to define an incident angle between the channel and the living creature.

In a next aspect, the incident angle of said medical device constitutes an angle of about 5-10°, in particular about 7°.

In a next aspect, the handling segment of said medical device is angled relative to the remaining parts of the retaining strap.

In a next aspect, the first side of said medical device comprises an adhesive material.

In some embodiments, the adhesive material may be selected from the list comprising: glue, tape or more generally an adhesive material.

In preferred embodiments, the first side of the body member may comprise an adhesive sheet which covers the entire surface of the first side of said body member. This way, the body member has a large amount of contact surface with the patient's skin in order for the body member to be tightly secured to a part of the patient's body. The adhesive sheet may be flexible such that it can conform to the shape of the patient's body. Furthermore, the adhesive sheet may also comprise an adhesive material, which may equally be selected from the list comprising: glue, tape or more generally an adhesive material.

In a next aspect, the retaining post and the retaining strap of said medical device is angled relative to the remaining parts of the retaining strap inhibit at least longitudinal movement of the medical article relative to the body member in the engaged position.

In a next aspect, use of said medical device for securing a catheter to a living creature is disclosed.

In a further aspect, a kit comprising said medical device, a medical article and optionally an adhesive foil is disclosed.

We now refer to FIG. 1, showing a perspective view of a medical device 1 in accordance with an embodiment of the present invention. In the current figure, the medical device 1 is disclosed in a disengaged position, meaning that a catheter (not shown) can be accepted by the medical device 1 (may also be referred to as: "placed within the medical device"). The medical device 1 comprises a body member 2 having a first side 3 for securing the medical device 1 to a person (e.g. an arm, the neck or the chest of a living creature) and a second side 4 opposite the first side 3. The body member 2 is slightly flexible such that it can conform to the shape of the living creature and can be removably coupled to the living creature using an adhesive material 16 (e.g. glue or tape). The adhesive material 16 may be connected to the first side 3 of the body member 2. The body member 2 is preferably made of a deformable solid material (e.g. thermoplastic elastomers or polyurethane based gel) which allows the body member 2 to at least partially conform to the living creature, and providing a sufficient amount of flexibility to the body member 2, such that the body member 2 is able to slightly deform in its entirety, for example when the patient is applying pressure on the medical device 1 by lying on the medical device 1. Because of this feature, the patient will experience noticeably less discomfort compared to medical devices consisting of stiff, non-deformable materials.

Moreover, the second side 4 of the body member 2 comprises a retaining post 5 having an abutment 50, a first channel portion 80 for accepting at least part of the luer-lock portion of a catheter and a supporting structure 11 for longitudinal movement inhibition as well as providing support at least for the catheter tubing.

Besides that, the medical device 1 comprises a retaining strap 6, which is attached to the body member 2. The retaining strap 6 comprises a handling segment 9, a second channel portion 81 and a retaining segment 10 having an opening 7. The second channel portion 81 cooperates with the first channel portion 80 to form a channel 8 (not shown) only when the medical device is manipulated in the engaged position. In the engaged position, the channel 8 will fully enclose at least part of the luer-lock portion of the catheter, effectuating a movement inhibition thereof. Furthermore, the channel 8 is angled according to an angle β (beta) relative to the longitudinal axis of the medical device 1 to define an incident angle β between the channel 8 and the living creature (e.g. the patient). More specifically, the channel 8 will exert an inward force upon the luer-lock portion in order to enable said movement inhibition. The handling segment 9 forms an angle according to an angle γ (gamma) with the retaining segment 10 in order to be able to better grab the handling segment 9. This is proven to be especially useful when the retaining strap 6 is in the engaged position, because of the small distance between the handling segment 9 and the person's skin. The fingers of the person operating the medical device 1 can more easily reach for said handling segment 9 in those situations.

Furthermore, the thickness of a central point 15 of the first channel portion 80 is disclosed on FIG. 1, measured from the first side 3 of the body member 2 to the second side 4 of the body member. This thickness is low enough to allow the medical device 1 to be slid underneath a medical article whenever this medical article is already attached to the patient. Also, whenever the medical device 1 should be replaced, the low thickness of said central point 15 allows for removal and replacement of said medical device 1 without having to remove the medical article from the patient. This, together with the fact that the medical device 1 allows for an easy securement, drastically reduces the risk of accidental removal of the medical article as well as medical article dislocation or migration. Furthermore, said replacement of the medical device 1 requires little time and can be executed safely by health professionals (e.g. a nurse or doctor).

Figure 2:
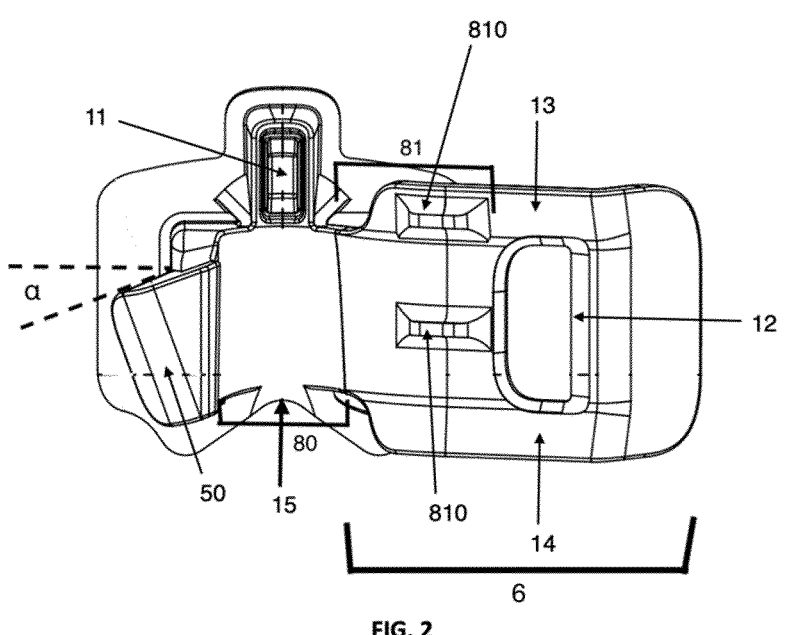
FIG. 2 is a top view of a medical device, according to an embodiment of the present invention.

We now refer to FIG. 2, showing a top view of a medical device 1 in accordance with an embodiment of the present invention. The second channel portion 81 is provided with two protrusions 810 which further inhibit the longitudinal movement of the catheter (not shown). To achieve this, the protrusions 810 exert an additional inward force upon the luer-lock portion of the catheter when the medical device 1 is in the engaged position. Furthermore, in some cases when at least a portion of a ribbed luer-lock is present within the channel 8, at least one protrusion 810 is able to contact at least one notch of the ribbed surface of the luer-lock. This creates an additional point of contact between the luer-lock and the medical device 1 resulting in a further longitudinal movement inhibition. In some cases, at least one protrusion 810 may extend in front of the luer-lock, being at the side of the catheter needle. This also realizes a further longitudinal movement inhibition.

Furthermore, an inner edge 12 of the opening 7 is adapted to hook behind the abutment 50 of the retaining post 5. This allows for a tight and secure fix of the retaining strap 7 in the engaged position when the medical article is correctly inserted within the medical device 1. The retaining strap 6 is also slightly deformable. Hence, when the retaining strap 6 is gripped and pulled at to be moved to the engaged position, the opening 7 of the retaining strap 6 slightly enlarges and is able to enclose the retaining post 5. Once released, the abutment 50 prevents the retaining strap 7 from returning to the disengaged position. This way, the retaining strap 6 is tightly held into place by the abutment 50.

The specific interaction between the abutment 50 and the inner edge 12 of the opening 7 is thus of great importance. This specific interaction can only be fully realized when the catheter is properly placed within the medical device 1. This serves as a safety feature when securing the catheter within the medical device 1, allowing the persons operating the device (e.g. a doctor or a nurse) to perform a self-control of their actions. Therefore, this specific interaction is an additional safety feature which further decreases the risk of complications for the patient.

Also, in this embodiment, the abutment 50 is angled in a horizontal plane according to an angle α (alpha) relative to the retaining post 5 causing the retaining strap 6 to exert an increased force (or "tension") upon the luer-lock portion of the catheter when the retaining strap 6 is in the engaged position. This leads to a further movement inhibition of the catheter within the medical device 1. The angled position a also slightly affects the form of the channel 8, creating a subtle conical shape. This conical shape allows a tighter fix of specific sizes of catheters resulting in a further movement inhibition thereof.

Figures 3, 4:
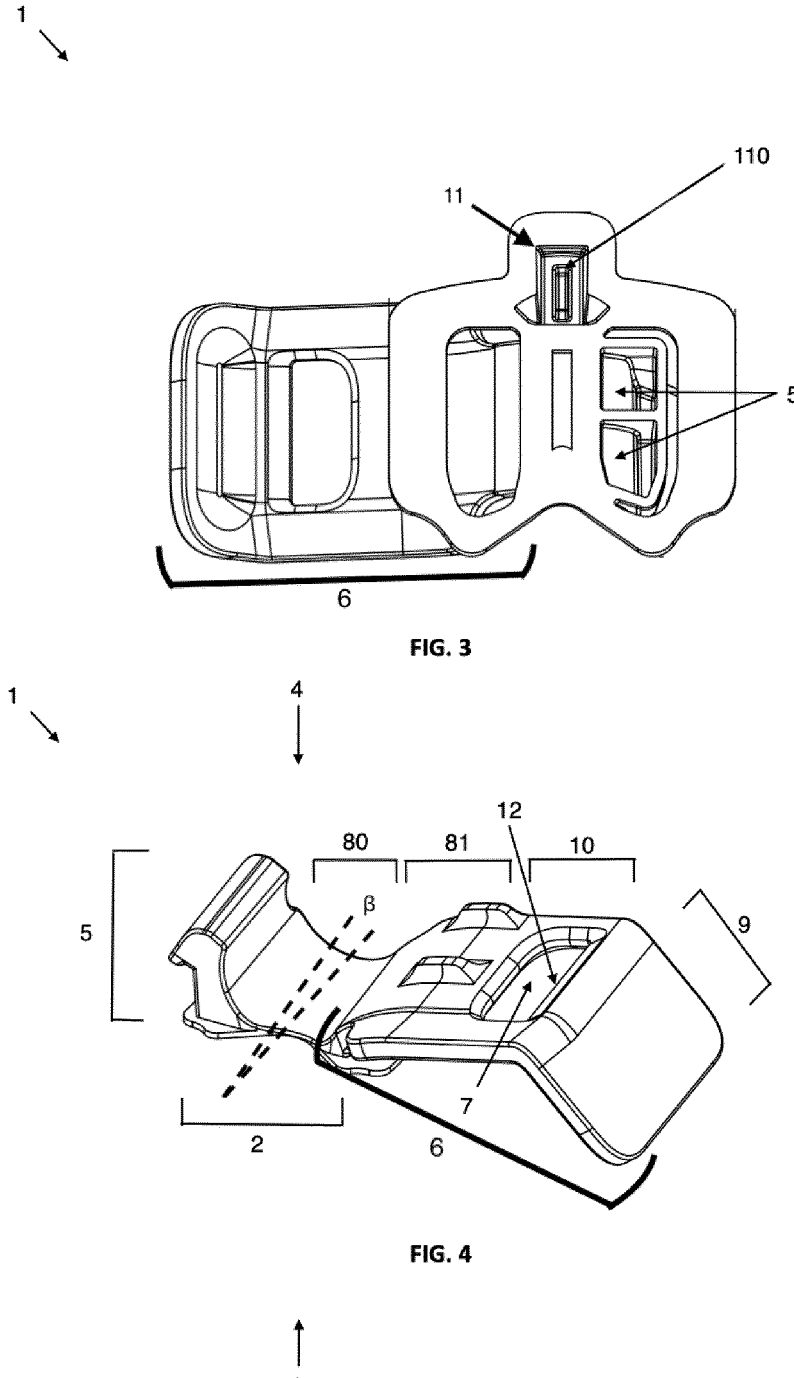
FIG. 3 is a bottom view of a medical device, according to an embodiment of the present invention.
FIG. 4 is a perspective view of a medical device, according to an embodiment of the present invention.

We now refer to FIG. 3, showing a bottom view of a medical device 1 in accordance with an embodiment of the present invention. The supporting structure 11 having a fluidum filled chamber 110 is shown. This supporting structure 11 supports the tubular part of the catheter when placed within the medical device 1. If a pulling force would be exerted upon the catheter, the supporting structure 11 further inhibits the longitudinal movement of the catheter. Additionally, it aids in preventing the catheter from tilting upwards in the direction of the second side 4 of the medical device 1. All of this reduces the risk of complications (e.g. phlebitis) when the medical article is fixed to the patient (e.g. needle inserted within the human body). The fluidum filled chamber 110 of the supporting structure 11 also enables a certain amount of compressibility, which allows catheters with a multitude of different tubing sizes to be placed within the medical device 1, since the supporting structure 11 mainly supports the tubular portions of the medical articles.

Also, the fluidum filled chamber 51 of the retaining post 5 is clearly visible, which enables the retaining post 5 to slightly deform and adapt to the form of at least a portion of the luer-lock when placed within the medical device 1. This equally enables a larger amount of medical articles having different luer-lock types and sizes to be secured within the medical device 1. It should be noted that luer-locks are often uneven in shape. Therefore, the ability of said fluidum filled chamber 51 to slightly deform is a great advantage compared to non-deformable alternatives.

Finally, FIG. 4 shows a perspective view of a medical device in accordance with an embodiment of the present invention. The medical device 1 according to this embodiment, however, does not comprise a supporting structure 11. Furthermore, the abutment 50 is not angled in a horizontal plane relative to the retaining post 5. Therefore, when this medical device 1 is manipulated in the engaged position, the channel 8 formed by the first and second channel portions (80, 81) is not conical but rather circular.

FIG. 5A is a front perspective view of a medical device 1 comprising a medical article, according to an embodiment of the present invention, wherein the medical device is in a disengaged position. This figure clearly visualizes the luer-lock portion 18 with a peripheral rim 19 of the medical article being located within the first channel portion 80 of the medical device 1. In this embodiment, the retaining post 5 of the medical device 1 comprises an abutment 50, said abutment 50 making an angle delta (δ) with the retaining post 5. This specific angle (δ) allows the user (e.g. nurse) to manipulate the retaining strap 6 into the engaged position by a mere sideways pulling motion of the retaining strap 6, avoiding most of the downward pulling motion which otherwise would be necessary in order for the opening 7 of the retaining strap 6 to enclose said retaining post 5. The avoidance of most of the downward pulling motion reduces the risk of pushing down the retaining post 5 while securing the retaining strap 6 in the engaged position. Pushing down the retaining post 5 might make it harder for the opening 7 of said retaining strap 6 to enclose said retaining post 5. A next advantage is the fact that the retaining strap is positioned further away from the base of the medical device. As such, there is more room between the base and the handling segment 9, making it easier to grab the handling segment 9 of the retaining strap 6 and bring said retaining strap 6 into the disengaged position.

FIG. 5B is a front perspective view of a medical device 1 comprising a medical article, according to an embodiment of the present invention, wherein the medical device 1 is in an engaged position and FIG. 5C is a rear perspective view of a medical device 1 comprising a medical article, according to an embodiment of the present invention, wherein the medical device 1 is in an engaged position. Both of these figures disclose the securement of a catheter comprising a luer-lock and a tubular portion, both supported by the medical device 1. As seen on FIG. 5A, both the first and second channel potions 80, 81 together form the channel 8 in which the luer-lock portion of the catheter is tightly held, inhibiting any movement of the catheter. This movement inhibition is further reinforced by the supporting structure 11, which supports the tubular portion of said catheter, as visualized on FIG. 5C. Furthermore, the medical device 1 in this embodiment comprises an extension structure 52 which further reduces the risk of any transversal movement of the medical article once secured within said medical device 1. As seen on FIG. 5C, said extension structure 52 forms an extension of the retaining post 5 towards the back side of the medical device 1, thereby providing further support of the medical article. Also, the top side 520 of the extension structure 52 is flattened towards the back side of the medical device 1. This flattened top side avoids any obstruction of the first part 13 of the retaining strap 6 when manipulated into the engaged position.

LIST OF FEATURES

| Number | Feature |
| --- | --- |
| 1 | Medical device |
| 2 | Body member |
| 3 | First side (of the body member) |

-continued

LIST OF FEATURES

| Number | Feature |
|---|---|
| 4 | Second side (of the body member) |
| 5 | Retaining post |
| 6 | Retaining strap |
| 7 | Opening |
| 8 | Channel |
| 9 | Handling segment |
| 10 | Retaining segment |
| 11 | Supporting structure |
| 12 | Inner edge |
| 13 | First part (of the retaining strap) |
| 14 | Second part (of the retaining strap) |
| 15 | Central point (of the first channel portion) |
| 16 | Adhesive material |
| 17 | Adhesive foil |
| 18 | Luer-lock portion (of the medical article) |
| 19 | Peripheral rim (of the medical article) |
| 50 | Abutment |
| 51 | fluidum filled chamber (of the retaining post) |
| 52 | extension structure |
| 80 | First channel portion |
| 81 | Second channel portion |
| 110 | Deformable fluidum filled chamber (of the supporting structure) |
| 520 | Top side of the extension structure |
| 810 | Protrusion |

The invention claimed is:

1. A medical device for securing a medical article to a living creature, the medical article containing a luer-lock, the medical device comprising:

a body member having:

a first side adapted to be removably attached to the living creature;

a second side opposite the first side, the second side provided with a retaining post; and a first channel portion; and a retaining strap attached to the body member, the retaining strap having:

a retaining segment comprising an opening, the opening being adapted to enclose at least part of the retaining post in an engaged position;

a handling segment for manipulating the retaining strap between a disengaged position and the engaged position;

a second channel portion;

wherein:

the first channel portion and the second channel portion cooperate to form a channel in the engaged position, the channel being adapted to receive at least a portion of the luer-lock;

the medical article and the retaining strap cooperate to retain the retaining strap in the engaged position; and the retaining post comprises a fluidum filled chamber.

2. The medical device according to claim 1, wherein the retaining strap is an integral part of the body member.

3. The medical device according to claim 1, wherein the retaining post further comprises an abutment angled in a horizontal plane relative to the retaining post.

4. The medical device according to claim 3, wherein the abutment grips behind an inner edge of the opening when the retaining strap is manipulated to the engaged position, retaining the retaining strap in the engaged position.

5. The medical device according to claim 1, wherein the retaining strap further comprises at least one protrusion exerting an inward pressure upon at least a portion of the luer-lock.

6. The medical device according to claim 1, further comprising a supporting structure having a deformable fluidum filled chamber, wherein the supporting structure is in line with the first channel portion to further support at least part of the medical article.

7. The medical device according to claim 1, wherein a tension exerted upon the medical article by the retaining strap is distributed over a first part and a second part of the retaining strap, and wherein a tension exerted by at least the second part aids in preventing an upward movement of the medical article.

8. The medical device according to claim 1, wherein a maximum thickness of a central point of the first channel portion is from about 0.5 mm to about 3 mm.

9. The medical device according to claim 1, wherein the channel is angled relative to a longitudinal axis of the medical device to define an incident angle between the channel and the living creature.

10. The medical device of claim 9, wherein the incident angle constitutes an angle of about 5° to about 10°.

11. The medical device of claim 9, wherein the incident angle constitutes an angle of about 7°.

12. The medical device according to claim 1, wherein the handling segment is angled relative to the remaining parts of the retaining strap.

13. The medical device according to claim 1, wherein the first side of the body member comprises an adhesive material.

14. The medical device according to claim 1, wherein the retaining post and the retaining strap inhibit at least longitudinal movement of the medical article relative to the body member in the engaged position.

15. A kit comprising the medical device of claim 1, a medical article, and optionally an adhesive foil.

* * * * *